United States Patent [19]
Langner

[11] Patent Number: 5,902,740
[45] Date of Patent: May 11, 1999

[54] PROCESS FOR THE DECONTAMINATION OF CELL CULTURES CONTAINING MYCOPLASMAS

[75] Inventor: Klaus-Dieter Langner, Marburg, Germany

[73] Assignee: Behringwerke Aktiengesellschaft, Marburg, Germany

[21] Appl. No.: 08/012,985

[22] Filed: Feb. 3, 1993

Related U.S. Application Data

[63] Continuation of application No. 07/528,133, May 24, 1990, abandoned.

[30] Foreign Application Priority Data

May 26, 1989 [DE] Germany .............................. 39 17 163

[51] Int. Cl.$^6$ ................................ C12N 5/06; C12N 5/08; A61K 31/70; C07H 19/167
[52] U.S. Cl. ........................ 435/240.2; 514/45; 536/27.8
[58] Field of Search .............................. 536/27.8; 514/45, 514/46; 435/240.3, 240.2

[56] References Cited

U.S. PATENT DOCUMENTS 4,387,161 6/1983 McGarrity et al. ........................ 435/34
4,895,803 1/1990 Hubner et al. ........................ 435/240.1

OTHER PUBLICATIONS

Ishiguro, K. et al., "Depletion of Mycoplasma from Infected Cell Lines By Limiting Dilution in 6–methylpurine deoxyriboside", Journal of Immunology, vol. 108, pp. 39–43, (1988).
L.B. Robinson et al., Science 124:1147 (1956).
G.J. McGarrity and D.A. Carson, Exp. Cell Res. 139:199–205 (1982).
R.J. Hay et al., Nature 339:487–8 (1989).
Hay et al. Nature 339:487–488, 1989.
Robinson et al. Science 124: 1147, 1956.
Schmidt et al. Exp. Cell Res. 152: 565–570, 1984.
McGarrity et al. Exp. Cell Res. 139:199–205, 1982.

*Primary Examiner*—Gary L. Kunz
*Attorney, Agent, or Firm*—Finnegan, Henderson, Farabow, Garrett & Dunner, L.L.P.

[57] ABSTRACT

The invention relates to a process for the decontamination of cell cultures containing mycoplasmas. In this process the cell cultures infected by mycoplasmas undergo an antibiotic treatment in a first step, and cells still infected are then eliminated by 6-methylpurine deoxyriboside solution in a second step.

5 Claims, No Drawings

PROCESS FOR THE DECONTAMINATION OF CELL CULTURES CONTAINING MYCOPLASMAS

This application is a continuation of application Ser. No. 07/528,133, filed May 24, 1990, now abandoned.

The invention relates to a process for the decontamination of cell cultures containing mycoplasmas. In this process the cell cultures infected by mycoplasmas undergo an antibiotic treatment in a first step, and cells still infected are then eliminated by 6-methylpurine deoxyriboside solution in a second step. Mycoplasmas are bacteria-like microorganisms which synthesize neither a cell wall nor a bacterial capsule. They grow both in cell cultures (cytoadsorbed) and in cell-free medium. Mycoplasmas typically require cholesterol and other steroid compounds.

The contamination of cell cultures by mycoplasmas is a widespread problem in cell technology. It was first reported by Robinson (L.B. Robinson et al., (1956), Science, 124, 1147). The average contamination rate now found in permanently growing cell cultures on the laboratory scale is approximately 15%. In industrial cultivation up to as many as 90% of all cultures may be infected by mycoplasmas. This represents an important problem for the biotechnological production of recombinant proteins, since pharmaceutical products which are synthesized in animal cells must be absolutely free from mycoplasma antigens.

The most important sources of infection are contaminated sera and already infected cell cultures. In most cases the transmission takes place by air-borne infection or aerosols. An infected culture contains between $10^6$ and $10^9$ colony forming units (CFU) per milliliter of conditioned medium without turbidity of the medium or a characteristic odour being detectable.

The presence of certain mycoplasma strains leads to degenerative effects in the cell culture caused by extensive acid production. The most frequently occurring mycoplasma strains such as M. arginini, M. orale, M. hyorhinis and A. laidlawii proliferate without morphological changes in the contaminated cell line. However, chromosome aberrations and a changed cell metabolism are often found in cultures contaminated with mycoplasmas.

In practice there are now a number of test systems available which can be used for the detection of a mycoplasma contamination. A simple and sensitive method of detection, also of non-cytoadsorbed mycoplasmas, is based on the cytotoxicity of 6-methylpurine derivatives mediated by mycoplasmas.

This cytotoxicity is caused by the enzyme adenosine phosphorylase which is synthesized in mycoplasmas but not in animal cells. In the presence of this enzyme 6-methylpurine deoxyriboside (6-MPDR) or 6-methylpurine riboside (6-MPR) are cleaved, and 6-methylpurine (6-MP) which is the cytotoxic substance is liberated (G. J. McGarrity, et al. (1982), Exp. Cell Research, 139, 199). Since even concentrations of less than 5 $\mu$M of the cleavage product 6-MP are toxic for the cells, the consequence is a lysis of the cell culture contaminated with mycoplasmas detected. Since all relevant strains of mycoplasmas contain adenosine phosphorylase, all possible sources of contamination are detected by this test system.

The decontamination of cultures containing mycoplasmas has hitherto been regarded as difficult and laborious. One possibility is passage of the contaminated culture in nude mice. This process is used for hybridoma cultures, but requires great technical elaboration. With other cell species (for example BHK cells) there is also the risk that cells may be lost in this procedure. An additional possibility is treatment with various antibiotics. There are a number of substances which are tolerated relatively well by animal cells and which can be used to remove the mycoplasmas, at least for a short period of time. However, ever, there is often only repression of growth of the various strains of mycoplasmas so that after a few passages the culture is contaminated again. Additionally there is the risk of development of resistance to the various antibiotics on repeated administration.

The invention accordingly relates to a process for the decontamination of cell cultures containing mycoplasmas, wherein antibiotics effective against mycoplasmas are used in a first step. In a further step the cells or cell clones still containing mycoplasmas are then eliminated by cultivation in the presence of 6-methylpurine deoxyriboside so that only the truly mycoplasma-free cells or cell clones remain, that is to say survive. Preferably Tiamulin™ and Minocycline™ are used as antibiotics and 6-methylpurine deoxyriboside is used in a concentration of 50 $\mu$M.

The invention also relates to mycoplasma-free cell cultures obtained in this way and to their use, in particular cular for the genetically engineered production of foreign proteins in these cells. The invention is additionally disclosed in the claims and the example.

EXAMPLE

Decontamination of Hamster Cells Containing Mycoplasmas

Rodent cells are a preferred system for the expression of heterologous recombinant proteins. CHO (Chinese hamster ovary) and BHK (baby hamster kidney) cells are most frequently used. Both cell lines are established cultures and are already being used for the industrial production of recombinant proteins.

BHK and CHO clones which secrete a particular protein (for example factor VIII:C or AT III) were isolated by a laborious process involving transfection, selection, and cloning. A mycoplasma contamination was detected in some of these clones.

To avoid repeating the time-consuming transfection and selection process yet again with mycoplasma-free cells, the following process was used for decontamination: first the contaminated cell cultures were alternately treated with the antibiotics thiamulin and minocycline (Sebio, concentration according to manufacturer's instructions) for 2 passages each. Then the cells were kept completely without antibiotics for 4 passages. After checking in the mycoplasma test, single clones of the mycoplasma-free cultures were obtained. For this cells were distributed on a 96-well plate in a cell density of 2 cells/well and 10 cells/well using limiting dilution. The use of 5 wells per dilution step for each culture had proved to be sufficient. After an initial growth phase of 1–2 days, 5 $\mu$l/well of a 1 mM 6-methylpurine deoxyriboside solution (6-MPDR) were added to each of the cultures (final concentration 50 $\mu$M/well). The cells were then incubated in this solution for 5–6 days (until they reached confluence).

Under these conditions cells which were still slightly contaminated with cytoadsorbed mycoplasmas died. The cells were then transferred to a 24-well plate and later to a 6-well plate and maintained without 6-MPDR.

After this treatment various mycoplasma tests were again carried out (microbiological cultivation and mycoplasma-mediated cytotoxicity). In the case of a negative result some of the clones were frozen and some were maintained in culture. After 5, 10, 15 and 20 passages in each case the cells were tested for mycoplasma contamination again, and all the cultures which were treated by the process described above were found to be negative without exception.

In parallel, the cells were treated only with the antibiotics described above, single clones were obtained and maintained not in the presence of 6-MPDR. The cells were then frozen and some were maintained in culture as controls. After 5, 10, 15 and 20 passages mycoplasma tests were again carried out, and in about 30% of the cultures mycoplasmas were again detectable after passage 10. This entailed the cells being maintained under conditions which ruled out reinfection with mycoplasmas.

This process was also used with human cell cultures (HeLa and KB cells) and with monkey cells (COS cells), with the same success.

I claim:

1. A process for the decontamination of animal and human cell cultures containing mycoplasmas, which comprises a) treatment with an antibiotic effective on mycoplasmas in an amount and for a time effective to substantially reduce the number of infected cells, b) subsequent cloning of the treated cells to obtain single clones, and c) subsequent treatment of the single clones with 6-miethylpurine deoxyriboside in an amount and for a time effective to eliminate residually infected cells.

2. The process of claim 1, wherein 6-methylpurine deoxyriboside is used at a final concentration of 50 $\mu$M.

3. The process of claim 1, wherein the antibiotic used is Tiamulin™, Minocycline™, or both Tiamulin™ and Minocycline™.

4. The process of claim 1, wherein the decontaminated cell lines are Chinese hamster ovary cells, baby hamster kidney cells, human Hela cells, human KB cells or monkey COS cells.

5. The process of claim 3, wherein the antibiotics Tiamulin™ and Minocycline™ are used alternately.

* * * * *